Jan. 15, 1974 D. L. ARMSTRONG Plant Pat. 3,438
ROSE PLANT
Filed March 21, 1972
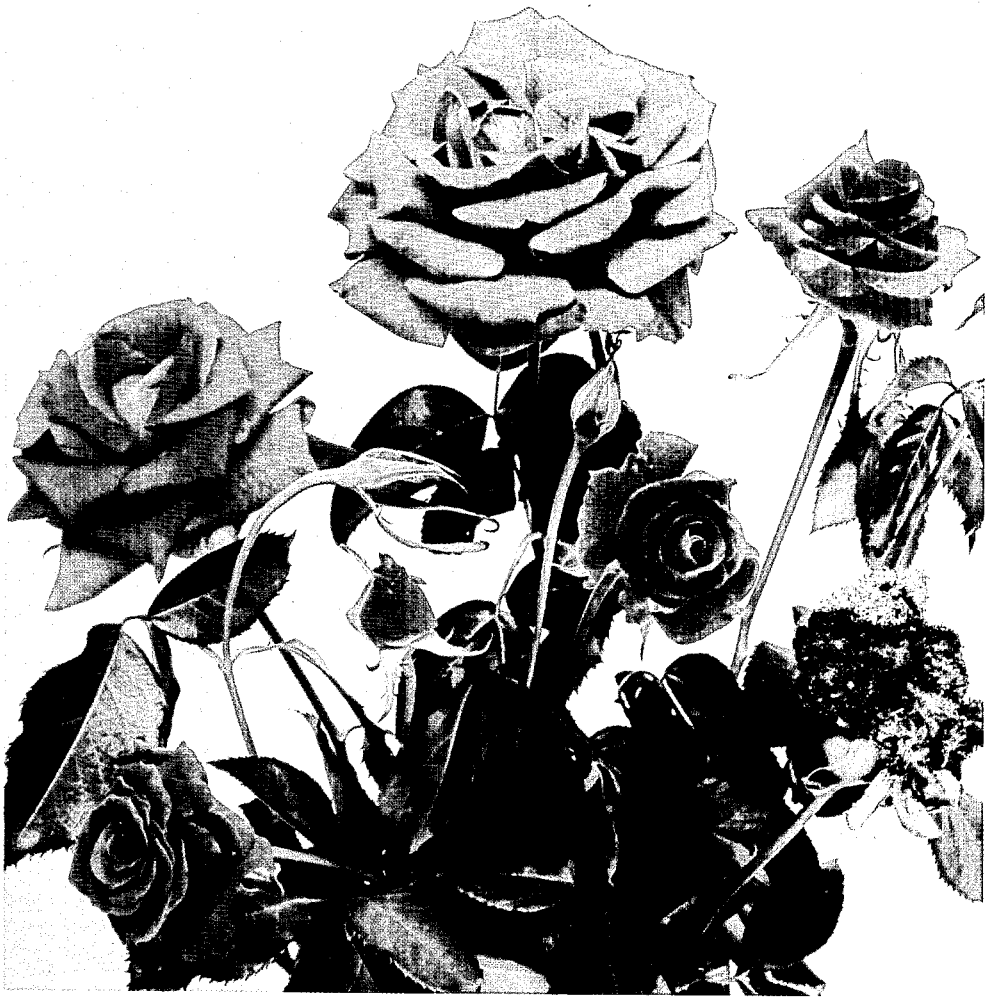

United States Patent Office

Plant Pat. 3,438
Patented Jan. 15, 1974

3,438
ROSE PLANT

David L. Armstrong, Upland, Calif., assignor to Armstrong Nurseries, Inc., Ontario, Calif.

Filed Mar. 21, 1972, Ser. No. 236,798
Int. Cl. A01h 5/00
U.S. Cl. Plt.—20 1 Claim

ABSTRACT OF THE DISCLOSURE

A bush seedling rose of the hybrid tea class, asexually reproduced by budding in Ontario, Calif. Flowers are of a light red color, range up to 5½" in diameter, and consist of 30 to 36 large petals with between 5 and 12 petaloids. The fragrance is moderate and mixed. The plant has large dark green foliage which is generally glossy and usually flat, though sometimes slightly troughed. The habit of growth is vigorous, moderately upright, and well-branched. The flowers usually are borne singly on peduncles and stems which are medium to large in length and caliper. Steady bloomer. Wet weather may delay or prevent opening of buds or cause peduncles to bend under weight of flowers.

This invention relates to a new variety of bush seedling rose of the hybrid tea class, grown outdoors for cut flowers and garden decoration. It was propagated and grown in Ontario, Calif.

The plant is a seedling having as its seed parent Manitou and as its pollen parent Grand Slam (Plant Pat. No. 2,187). It holds its distinguishing characteristics through succeeding propagations by budding.

The accompanying drawing illustrates the plant in color and shows the flowering thereof from bud to full bloom.

This new variety may be distinguished from its seed parent, Manitou, in the following characteristics:

The flowers of this new variety manifest substantially less yellow at the base of the petals than do the flowers of Manitou, as well as less yellow in the underlying color of the flowers.

The plant of this new variety is substantially more erect than that of Manitou. The foliage is generally of a darker green color and of a harder substance than that of Manitou, the leaves having more breadth in relation to length than in Manitou. Additionally, the serrations of this new cultivar are more deeply cut and much coarser in character.

Whereas, in this new cultivar there is a frequent proliferation of vegetative malformation in the sexual parts of the flower, particularly when the plants are young or responding to fertilization, this characteristic is seldom found in the cultivar Manitou.

This new cultivar is distinguished from its pollen parent, Grand Slam, in the following respects:

The foliage of this new cultivar is much larger than that of its pollen parent, and is more glossy and dark green, as contrasted with the non-glossy gray-green character of the foliage of Grand Slam.

Whereas the plant of Grand Slam is somewhat spreading and irregular in habit, this new cultivar tends to be more upright and regular in growth.

The peduncles of this new cultivar tend to be much thicker in caliper than those of Grand Slam, and the receptacles are characteristically more prominent and larger.

Whereas the flowers of this new cultivar tend strongly to have prominent foliaceous sepals, this seldom occurs in Grand Slam.

The flower color of this new cultivar is described in popular terms as light red (American Rose Society classification) whereas the flowers of Grand Slam are described as medium red, a substantially deeper tone.

The flower petals of this new cultivar are substantially broader and the flowers are larger than those of Grand Slam.

The flowers of this new variety are usually borne singly on normal to strong, medium to long stems. The plant blooms abundantly outdoors and moderately in the greenhouse, and nearly continuously during the growing season. The fragrance is moderate and mixed.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is average to very long in length, of average to heavy caliper, and may be bending or erect. Its color is near Strong Yellow Green, 2.5GY 6/8, and may be smooth or with from few to numerous stipitate glands.

Before the calyx breaks, the bud is medium in size, medium-length to long, pointed and ovoid.

As the calyx breaks, the color is near Strong Purplish Red, 10RP 4/12.

A fine wooly tomentum lines the inner surface of the sepals and the margins of alternate sepals. The margins of other sepals have some stipitate glands and foliaceous appendages, the tips of some sepals having foliaceous parts measuring up to one and one-half times the bud length.

As the first petal opens, it is average to large in size, of medium length to long, ovoid and pointed. The outer surface of the petal is between Strong Purplish Red, 7.5RP 4/11, and Strong Purplish Red, 10RP 4/12. The inner surface is near Strong Purplish Red, 10RP 4/12.

The bud opens up well, and is not prevented from opening by cold, hot, or dry weather. Wet weather may delay or prevent opening of the bud.

BLOOM

When fully open, the bloom is average to large in size, being from 3½" to 5½" in diameter. The petalage is from double to very double, with from 30 to 36 petals, plus between 5 and 12 petaloids which are arranged irregularly.

The form of the bloom is high-centered at first, becoming open and from cupped to high-centered later. At first, the petals remain somewhat tightly cupped, with tips rolled gently outward, becoming later, at maturity, more loosely cupped, with the tips still rolled outward.

The petals are medium to thick in texture, with the inside satiny and the outside slightly shiny to satiny. The outside and intermediate petals are broadly obovate, the intermediate petals sometimes having 1 or 2 notches. The inside petals are generally obovate, but sometimes irregular, and with from none to several notches. Their colors may be modified by being bordered, shaded and/or washed with other colors.

The following description applies to a newly opened flower grown in a greenhouse in the month of October, in Ontario, Calif.:

The outer surface of the outside petal is near Brilliant Greenish Yellow, 7.5Y 9/8, at the base, and becoming between Strong Purplish Red, 7.5RP 4/11, and Strong Purplish Red, 10RP 4/12. The inside surface of the outside petal is also near Brilliant Greenish Yellow, 7.5Y 9/8, at the base, becoming near Strong Purplish Red, 10RP 4/12.

The outer surface of the intermediate petal is near Brilliant Greenish Yellow, 7.5Y 9/8, at the base, becoming a color brighter than and between Deep Purplish Pink, 7.5RP 6/12, and Strong Purplish Red, 10RP 4/12. The inner surface of the intermediate petal is also near Brilliant Greenish Yellow, 7.5Y 9/8, at the base, but becoming a color more vivid than but between Strong Purplish Red, 10RP 4/12, and Strong Purplish Red, 7.5RP 5/12.

The outer surface of the inner petal is near Brilliant Greenish Yellow, 7.5Y 9/8, at the base, becoming a color more vivid than but between Deep Purplish Pink, 7.5RP 6/12, and Strong Purplish Red, 10RP 4/12. The inside surface of the inner petal is also near Brilliant Greenish Yellow, 7.5Y 9/8, at the base, but becomes a color more vivid than one between Strong Purplish Red, 10RP 4/12, and Strong Purplish Red, 7.5RP 5/12.

The description which follows was made from a rose that was open for three days in a greenhouse, in the month of October in Ontario, Calif.:

The outer surface of the outside petal was near Brilliant Greenish Yellow, 7.5Y 9/8, at the base, becoming near Strong Purplish Red, 7.5RP 5/12, overlaid in places with near Deep Purplish Pink, 5RP 6/10. The inner surface of the outside petal was also near Brilliant Greenish Yellow, 7.5Y 9/8, at the base, but soon becoming near, but more vivid than, Strong Purplish Red, 7.5RP 5/12.

The outer surface of the inside petal was near Brilliant Greenish Yellow, 7.5Y 9/8, at the base, becoming a color more vivid than but between Strong Purplish Red, 7.5RP 5/12, and Deep Purplish Pink, 5RP 6/10. The inner surface of the inside petal was also near Brilliant Greenish Yellow, 7.5Y 9/8, at the base, becoming near, but more vivid than, Strong Purplish Red, 7.5RP 5/12.

The general color effect of the newly opened flower is more vivid than near Strong Purplish Red, 10RP 4/12. After the bloom has been three days open, the color is more vivid than but near Strong Purplish Red, 7.5RP 5/12.

The petals of this new variety may persist, and are not particularly affected by cold, hot, wet, or dry weather.

In Southern California, the flower persists on the bush in the garden from three to five days in the month of October. Roses grown outdoors, but kept indoors at living-room temperatures, persist from three to five days in the month of October. Cut roses grown in the greenhouse, and kept at living-room temperatures, persist from three to four days in the month of October.

REPRODUCTIVE ORGANS

Stamens: The stamens are few to average in number, arranged irregularly about the pistils, a few being mixed with petaloids or sometimes tucked in the calyx.

Filaments: The filaments are medium-length to long, from 8 to 15 mm. Their color is near Vivid Greenish Yellow, 7.5Y 8/12. Most are with anthers.

Anthers: The anthers are medium size, opening at various times. Before shedding pollen, the color on both the upper and under sides is near white, with margins between Moderate Orange Yellow, 10YR 8/10, and Strong Orange Yellow, 10YR 7/10.

Pollen: The pollen is sparse, and between Moderate Orange Yellow, 10YR 8/10, and Strong Orange Yellow, 10YR 7/10, in color.

Pistils: The pistils are many, being approximately 150 in number.

Styles: The styles are moderately uneven, and have a color ranging from near Brilliant Greenish Yellow, 7.5Y 9/8, to near Strong Red, 2.5R 5/12.

Stigma: The stigma is near Brilliant Greenish Yellow, 7.5Y 9/8, in color.

Ovaries: Some ovaries are enclosed in the calyx, but most protrude from the calyx in an irregular manner, becoming more pronounced as the petals die.

Hips: The hips are average in length and globular, moderately smooth, with thick, fleshy walls. At three-quarters maturity, their color is between Dark Greenish Yellow, 10Y 6/7, and Strong Orange Yellow, 10YR 7/10. Very often, especially in the greenhouse, an irregular extension of the pistils "billows" out from the top of the hip forming a growth up to several times larger than the hip itself.

Sepals: The sepals are permanent, medium-length, and irregularly curled. On the inside, their color is near Moderate Brown, 7.5YR 4/5, overlaid with a brownish gray tomentum. The outside color is near Strong Brown, 5YR 4/5.

Seeds: There are few (from none to four) medium-sized seeds.

FOLIAGE

The compound leaves usually comprise from 3 to 7 leaflets, which is considered normal. They are large, somewhat leathery, and glossy to semi-glossy. The leaflets are oval to broadly lanceolate, with apex acute, base obtuse, and margin irregularly serrate.

The color of the mature foliage on the upper surface is between Moderate Olive Green, 5GY 4/3, and Grayish Olive Green, 5GY 3/2. The under surface is grayer than Moderate Yellow Green, 5GY 5/6.

The young growth is near Moderate Olive Green, 2.5GY 4/3, on its upper surface, very heavily overlaid with near Dark Red, 2.5R 3/7. The under surface is near Dark Greenish Yellow, 10Y 6/7, also very heavily overlaid with near Dark Red, 2.5R 3/7.

The rachis is average in size, the upper side being grooved, with many stipitate glands on the edges, the under side being sparsely prickly, and with stipitate glands.

The stipules are medium-length to long, medium-width, with medium-length points turning out at an angle of usually less than 90°, recurved toward the stem.

The plant has an average subjection to mildew.

GROWTH

The plant is bushy, moderately upright, and from much to moderately branched. Its growth is moderately vigorous, and the canes are from medium caliper to heavy.

The main stems are near Moderate Yellow Green, 5GY 5/6, in color, and bear several medium-length to long large prickles. These large prickles are hooked slightly downward, and have medium-length moderately narrow bases. There are several small prickles. The color of both the large and the small prickles ranges from near Brownish Orange, 5YR 5/8, to near Moderate Reddish Brown, 2.5YR 3/3. There are no hairs.

The branches are between Moderate Yellow Green, 5GY 5/6, and Strong Yellow Green, 5GY 6/8, in color, and bear from few to several medium-length to long large prickles. These large prickles are hooked slightly downward and have medium-length moderately narrow bases. Their color ranges from between Dark Yellow, 5Y 6/7, and Moderate Yellow Green, 2.5GY 5/5, to between Moderate Reddish Brown, 2.5R 3/3, and Strong Brown, 5YR 4/5. There are a few small prickles with a color ranging from Dark Yellow, 5Y 6/7, to between Moderate Reddish Brown, 2.5R 3/3, and Strong Brown, 5YR 4/5. There are no hairs, but some stipitate glands.

New shoots are near Strong Yellow Green, 2.5GY 6/8, in color, lightly to heavily overlaid with near Dark Red, 5R 3/7. There are few to several large prickles which are medium-length, hooked slightly downward, and having medium-length moderately narrow bases. Their color is near Moderate Yellow Green, 2.5GY 5/5, heavily overlaid with between Dark Red, 5R 3/7, and Dark Red, 2.5R 3/7. There are a few small prickles which have the same coloration as the large prickles. There are no hairs, but a few to many stipitate glands.

Unless otherwise stated herein, the information for this description was gathered from plants grown in a greenhouse in Ontario, Calif.

I claim:

1. An asexually reproduced hybrid tea rose plant, substantially as herein shown and described, the same being further characterized in a plurality of combinations of features, selected from the following: the production of blooms of a generally light red color, ranging from 3½" to 5½" in diameter with from 30 to 36 very large and broadly obovate, well-imbricated petals, each rolled gently outward, and from between 5 and 12 petaloids, said blooms being high-centered at first but some becoming slightly cupped as the flower opens; said petals being of moderate to heavy thickness with satiny interior and slightly shiny to satiny outer surface; said blooms, furthermore, usually being borne singly on normal to strong stems of medium length and on peduncles of medium to long length and medium to large caliper, with stipitate glands on the surface, the buds being of average to large size, of medium length, and of long pointed shape with sepals having foliaceous parts measuring up to one and one-half times the length of the bud; said plant further being of moderately vigorous growth with abundant dark-green foilage, and of moderately upright habit, well-branched and having canes of medium to large caliper.

No references cited.

ROBERT E. BAGWILL, Primary Examiner